US010487048B2

(12) United States Patent
Ranade et al.

(10) Patent No.: US 10,487,048 B2
(45) Date of Patent: Nov. 26, 2019

(54) CONFIGURATION AND ITS USE IN PROCESS FOR SYNTHESIS OF ALKYL CARBAMATES FROM ALKYL ALCOHOL AND UREA IN A TUBULAR REACTOR

(71) Applicant: COUNCIL OF SCIENTIFIC & INDUSTRIAL RESEARCH, New Delhi (IN)

(72) Inventors: Vivek Vinayak Ranade, Pune (IN); Ashutosh Anant Kelkar, Pune (IN); Vilas Hari Rane, Pune (IN); Anil Kisan Kinage, Pune (IN); Dhananjay Ravindra Mote, Pune (IN); Savita Kiran Shingote, Pune (IN); Lalita Sanjib Roy, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/558,072

(22) PCT Filed: Mar. 11, 2016

(86) PCT No.: PCT/IN2016/050084
§ 371 (c)(1),
(2) Date: Sep. 13, 2017

(87) PCT Pub. No.: WO2016/147204
PCT Pub. Date: Sep. 22, 2016

(65) Prior Publication Data
US 2018/0079714 A1    Mar. 22, 2018

(30) Foreign Application Priority Data
Mar. 13, 2015 (IN) .......................... 0678/DEL/2015

(51) Int. Cl.
*C07C 269/00* (2006.01)
*C07C 68/00* (2006.01)
*B01J 19/24* (2006.01)

(52) U.S. Cl.
CPC .......... *C07C 269/00* (2013.01); *B01J 19/2415* (2013.01); *C07C 68/00* (2013.01); *B01J 2219/00051* (2013.01); *B01J 2219/24* (2013.01)

(58) Field of Classification Search
CPC ....... C07C 269/00; C07C 68/00; B01J 19/242
See application file for complete search history.

(56) References Cited

U.S. PATENT DOCUMENTS 6,392,078 B1 * 5/2002 Ryu ........................ C07C 68/00
558/277
7,074,951 B2 * 7/2006 Ryu ........................ C07C 68/00
558/262

FOREIGN PATENT DOCUMENTS

WO    WO2014072803    *  5/2014

OTHER PUBLICATIONS

Liu et al, machine translation of CN Pat. No. 103254101, pub. Aug. 21, 2103, p. 1-13 (Year: 2013).*

* cited by examiner

*Primary Examiner* — Karen Cheng
(74) *Attorney, Agent, or Firm* — Seyfarth Shaw LLP

(57) ABSTRACT

The present invention discloses an improved catalyst free process for synthesis of alkyl carbamates in an integrated system comprising a tubular reactor and a striper. The process comprises reacting urea and an alcohol in said tubular reactor under autogeneous pressure; wherein said process provides >90% selectivity towards alkyl carbamate. The mixture of urea and alcohol is N fed to the tubular reactor at a particular feed rate. The tubular reactor is heated externally under autogeneous pressure to carry out a synthesis reaction producing alkyl carbamate and ammonia. The ammonia is removed from the tubular reactor by the striper. The tubular reactor and the stripper are arranged in series to reduce the equilibrium limitations of the reaction and drive the reaction in forward direction.

9 Claims, 1 Drawing Sheet

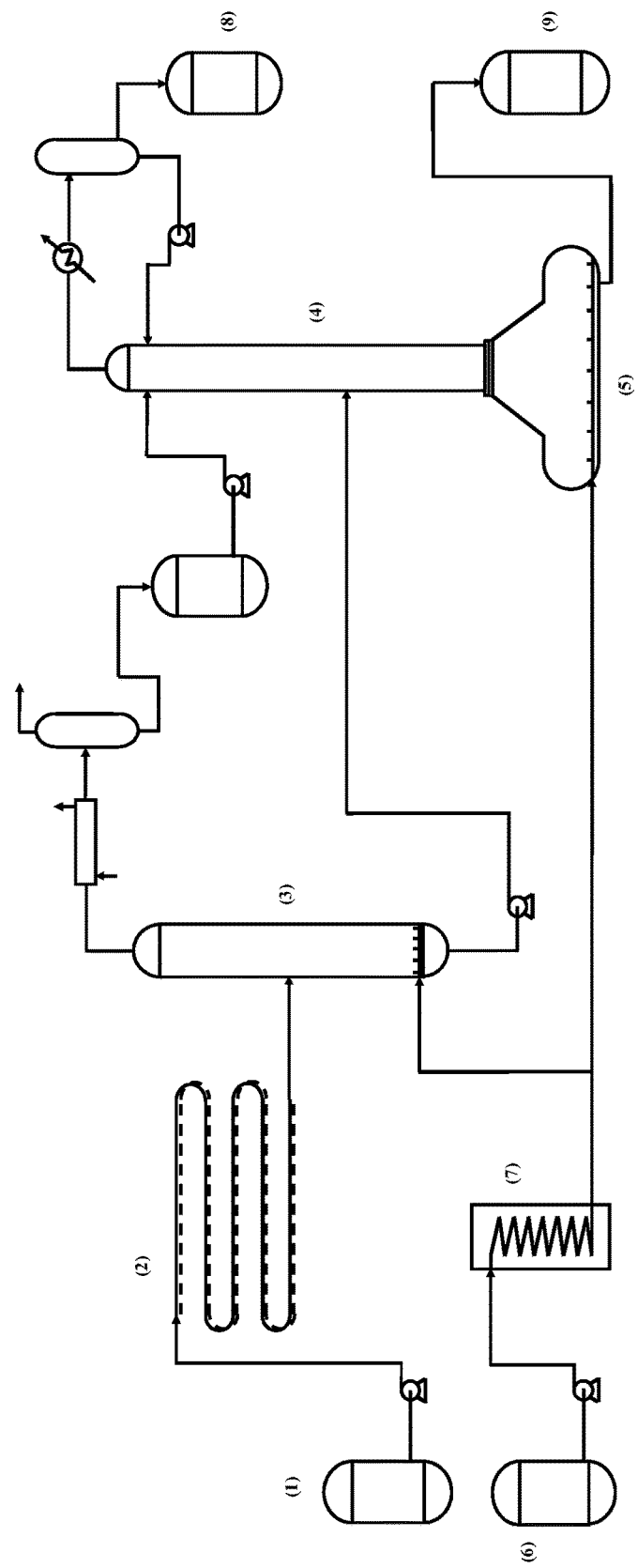

CONFIGURATION AND ITS USE IN PROCESS FOR SYNTHESIS OF ALKYL CARBAMATES FROM ALKYL ALCOHOL AND UREA IN A TUBULAR REACTOR

FIELD OF THE INVENTION

The present invention relates to an improved catalyst free process for synthesis of alkyl carbamates in a tubular reactor with simple configuration and to the tubular reactor with said configuration/integrated system thereof.

BACKGROUND OF THE INVENTION

Dimethyl carbonate (DMC) is an important intermediate and is widely used in industry. Owing to its low toxicity, dimethyl carbonate is considered a "green" chemical product with bright development prospects. This increasing focus is mainly due to the bio-degradability, with a low bioaccumulation as well as its low toxicity. Significant amount of work is being carried out to develop environmentally safer route for the synthesis of DMC.

Dialkyl carbonates like dimethyl carbonate (DMC), diethyl carbonate (DEC), dipropyl carbonate (DPC), dibutyl carbonate (DBC) are having potential applications in lithium battery as an electrolyte and can be prepared from urea and corresponding alkyl alcohol. In all cases first step will be the conversion of urea and alkyl alcohol to corresponding carbamate derivative. This is a non-catalytic equilibrium limited reaction. The conventional processes use stirred reactors which often limit the conversion and adversely influence selectivity.

Alkyl carbamate (for example methyl carbamate MC) synthesis by urea alcoholysis has been reported in literature with both catalytic/non-catalytic routes. The non-catalytic processes known in the art for urea alcoholysis however produced low yields of carbamates since these are equilibrium reactions. The further developments used tubular reactors using catalyst to enhance the conversion rate as well as yield.

In literature several reactor configurations have been reported for this reaction mostly operating in batch, semi batch mode in stirred vessel type of reactors.

U.S. Pat. No. 8,338,634 discloses a method for the synthesis of alkyl carbamates by reacting urea with a hydroxyl group containing compound in the presence of a catalyst. The catalyst comprises of a catalytically active component and a catalyst support. The reaction is carried out in a reactor, which may be a tubular reactor. The reaction may be continuous, semi-continuous or batch-wise. The ammonia formed during the reaction is removed from the reactor by appropriate means to shift the reaction equilibrium to the product side.

US20150315134 discloses a process for synthesis of methyl carbamate and dimethyl carbonate (DMC) in a reactor. The urea and methanol or methyl carbamate and methanol are fed into a reactor. The feed are put into a reactor vessel containing expanded slurry bed of solid catalyst particles suspended in a suspension liquid or in a packed bed of solid catalyst.

Since the synthesis of alkyl carbamates using urea and alcohol is a reversible reaction the equilibrium conversion depends on the alcohol to urea mole ratio. If byproduct ammonia is removed from the reaction mixture the equilibrium conversion is increased further. If sufficient alcohol to urea mole ratio is provided substantial urea conversion can be attained without removing ammonia.

The present inventors observed that there is a scope to provide urea alcoholysis reaction in a tubular reactor with simplified configuration/integrated system, in catalyst free environment, with near complete conversion of urea by stripping the ammonia formed and thus removing the equilibrium limitation.

OBJECTIVE OF THE INVENTION

It is therefore the primary object of the present invention to provide a catalyst free process for synthesis of alkyl carbamate using a simple, integrated tubular system that drives the reaction in the forward direction and reduces the equilibrium limitation of the reaction.

The other object is to provide a tubular reactor for synthesis of alkyl carbamate with easy to operate configuration/integrated system and enhancing the performance of the reaction.

Yet another objective is to synthesize further the di-alkyl carbonates, a useful intermediate.

SUMMARY OF THE INVENTION

Accordingly, the present invention provides a catalyst free process for synthesis of alkyl carbamate within an integrated system of at least one tubular reactor and a stripper in series, comprising reacting urea and an alcohol in said tubular reactor under autogeneous pressure; wherein said process provides >90% selectivity towards alkyl carbamate.

In an another embodiment, wherein a tubular reactor with a novel, simple configuration/integrated system for a catalyst free process for the synthesis of alkyl carbamate comprising at least one tubular reactor, heated externally, for reacting urea and alcohol and a stripper for removal of ammonia formed during the said process, wherein said tubular column and said stripper are arranged in series to attain equilibrium conversion.

In still another embodiment of the present invention, wherein the tubular rectors of the present invention provide adequate residence time to drive the reaction in the forward direction and achieve equilibrium conversion.

In yet another embodiment, wherein the present invention provides further synthesis of dialkyl carbonates by reacting the alkyl carbamate so formed with an alcohol in said integrated tubular system.

In an preferred embodiment of the present invention, wherein the alcohol is selected from methanol, ethanol, 1-propanol, 2-propanol, 1-butanol, 2-butanol, tert-butanol, pentanol and its isomers, hexanol and its isomers, their higher homologues or their isomers.

In another preferred embodiment of the present invention, wherein the temperature of the reaction mixture is in the range of 150-250 C In still another embodiment of the present invention, wherein urea and alcohol in mole ratio 10 to 50 are fed in to the tubular reactor at a feed rate of 5-25 ml/min.

In yet another embodiment of the present invention, wherein said process can be carried out continuously, semi continuously or batch wise.

In an another embodiment of the present invention, wherein the process further comprises reacting said alkyl carbamate with an alcohol to obtain dialkyl carbonate in said integrated system.

In still another embodiment of the present invention, wherein an integrated system for a catalyst free process for the synthesis of alkyl carbamate comprising at least one tubular reactor, heated externally, for reacting urea and alcohol and a stripper for removal of ammonia formed during the said process, wherein said tubular reactor and said stripper are arranged in series to reduce the equilibrium limitations of the reaction and drive the reaction in forward direction.

In an embodiment of the present invention, wherein the integrated system further comprises DMC reactor, wherein said alkyl carbamate obtained is reacted with alcohol vapours to obtain di alkyl carbonates.

In yet another embodiment of the present invention, wherein the diameter of the tubular reactors is ½' and the length is in the range of 4 to 9 meters to achieve adequate residence time and high conversion rate of urea.

In still another embodiment of the present invention, wherein the temperature of the tubular reactor is in the range 150-250° C.

BRIEF DESCRIPTION OF THE DRAWINGS

FIG. 1 depicts the configuration of tubular reactor—stripper.

DETAILED DESCRIPTION OF THE INVENTION

The invention will now be described in detail in connection with certain preferred and optional embodiments, so that various aspects thereof may be more fully understood and appreciated.

The present invention discloses reaction process for synthesis of alkyl carbamate using urea and alcohol in a catalyst free environment and in an integrated system comprising a tubular reactor, wherein said tubular reactor is sized in such a way that it provides adequate residence time for the reaction to complete and achieve equilibrium conversion. Further, the tubular reactors are provided with stripper in series such that the ammonia formed during the reaction is drawn out under reduced pressure which enables the reversible reaction to proceed in the forward reaction and eliminates the excess use of the raw material thereby making the process cost effective.

In the first embodiment, the present invention relates to a catalyst free process for synthesis of alkyl carbamate within an integrated system of at least one tubular reactor and a stripper in series, comprising reacting urea and an alcohol in said tubular reactor under autogenous pressure; wherein said process provides >90% selectivity towards alkyl carbamate.

The process of the present invention further comprises synthesis of di-alkyl carbonates, a useful intermediate, by reacting the alkyl carbamate formed with an alcohol in a DMC reactor column of the integrated system with a stripper in series.

In an optional embodiment, the process comprises reacting said alkyl carbamate and said di-alkyl carbonate in an additional tubular reactor with a stripper in series of the integrated system to obtain alkyl-N-alkyl carbamate with removal of carbondioxide and an alcohol which can be recycled/reused.

The alcohol can be selected from, but is not limited to, methanol, ethanol, 1-propanol, 2-propanol, 1-butanol, 2-butanol, tert-butanol, pentanol and its isomers, hexanol and its isomers, their higher homologues or their isomers.

The reaction for the synthesis of alkyl carbamates can be carried out continuously, semi-continuously or batch-wise.

The order of the addition of the raw materials to the reactor is not critical, and the best way to add the material can be determined in orienting experiments. Furthermore, the ammonia formed during the reaction is removed from the tubular reactor using stripper arranged in series continuously or intermittently to shift the reaction equilibrium to the product side.

In an embodiment, the reaction of urea and alcohol can be performed in a single tubular reactor or in multiple tubular reactors for complete conversion of urea with 95% selectivity towards Alkyl carbamates in a residence time of less than an hour.

The temperature of the process in the tubular reactor for synthesis of alkyl carbamate is maintained at 150-250° C., preferably 160-200° C. under autogenous pressure of about 5-30 bar.

The ingredients urea and alcohol are fed in to the tubular reactor at a feed rate of 5-25 ml/min to obtain alkyl carbamate. The mole ratio of urea to alcohol is in the range of 10 to 50.

The temperature for preparation of di-alkyl carbonate is in the range of 150 to 200° C. and pressure maintained with help of Back pressure regulator is in the range of 15 to 30 bar.

The tubular reactors can be of the material that can withstand the parameters of the reaction process without corrosion, crumbling and no reactivity towards the raw material used. Typically, the tubular reactors are sized in such a way that it provides adequate residence time and achieves equilibrium conversion. The dimensions of the tubular reactor are preferably 0.5 inch in diameter and 4 m-9 m in length.

In another embodiment, the present invention provides a configuration/integrated system wherein second stripper can be avoided, or second reactor can be attached to the reactor for the synthesis of Di alky carbonate in the next step.

Accordingly, referring to FIG. 1, the integrated system of the present invention comprises:

A urea feeding tank (1) connected to the Methyl carbamate reactor or tubular reactor (2), joining to the stripper (3) and a methanol holding/feeding tank (6), connected to an evaporator (7), leading to a connection to the stripper (3).

In another embodiment, the catalyst free process for the synthesis of alkyl carbamate using an integrated system comprising at least one tubular column and a stripper in series, comprises the steps of:

a. Dissolving urea into methanol to obtain homogeneous mixture solution;

b. Pumping the mixture of step (a) into a tubular reactor of ½" outer diameter and 4-9 m in length with the help of HPLC pump at a temperature maintained in the range of 170 to 180° C. at a feed rate in the range of 2-25 ml/min for a period of about an hour; Maintaining the pressure of the reactor of step (b) in the range of 15-30 bar with the help of a back pressure regulator mounted downstream of tubular reactor and collecting the desired carbamate and c. Stripping the ammonia through the stripper arranged in series with tubular reactor.

In an embodiment, the present invention provides a process wherein the urea conversion is >50% and alkyl carbamate selectivity is >80%; preferably >92%

The above process is shown below in Scheme 1:

Scheme: 1

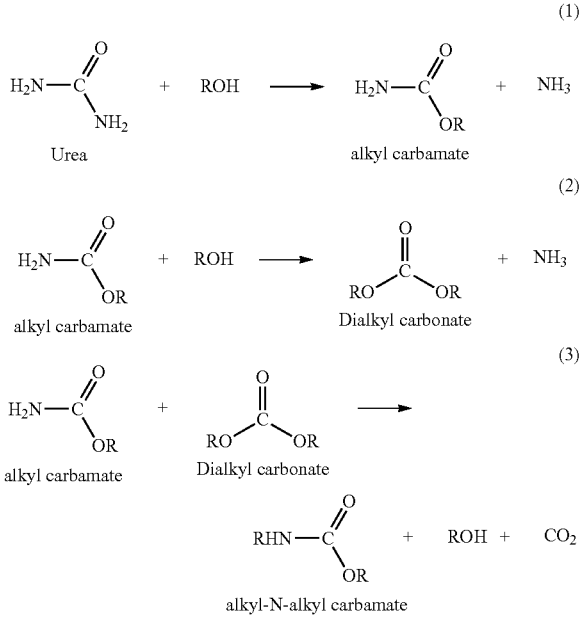

Where R = CH$_3$, C$_2$H$_5$, C$_3$H$_9$, C$_4$H$_{10}$

The disclosed arrangement is shown in FIG. 1. Urea is dissolved in alcohol in the urea—methanol feed vessel (1). The mixture is fed to the tubular reactor (2) at a particular feed rate. The tubular reactor (2) is heated externally under autogenous pressure to carry out a synthesis reaction producing alkyl carbamate and ammonia. The ammonia is removed from the tubular reactor (2) by means of the striper (3). The tubular reactor (2) and the stripper (3) are arranged in series to reduce the equilibrium limitations of the reaction and drive the reaction in forward direction. Alkyl carbamate obtained from the tubular reactor (2) is reacted with alcohol vapors in the DMC reactor (5) to obtain dialkyl carbonates. The alcohol vapors are obtained from the DMC reactor (5), arranged below the reactive distillation column (4), where the superheated alcohol is received from the alcohol feed vessel (6) and heated by the alcohol preheater and vaporizer (7). Dialkyl carbonate produced in the reaction in the distillation column (4) is collected in the top vessel (8) whereas the by products produced are collected in the bottom vessel (9).

The simple and stable configuration of the integrated system comprising of at least one tubular reactor of said dimensions and stripper arranged in series to remove the ammonia formed during the production of alkyl carbamate from urea and alcohol provides adequate residence time for the reaction to go to completion by reducing the equilibrium limitations and driving the reaction in forward reaction to achieve >90% selectivity towards alkyl carbamate.

The alkyl carbamate produced by the process of the present invention can be used in the synthesis of isocyanates, urethane foams, coatings, as pesticides and insecticides.

The dialkyl carbonates obtained as intermediates in the further embodiment of the process find application as electrolytes in Lithium batteries, solvents etc.

The following examples, which include preferred embodiments, will serve to illustrate the practice of this invention, it being understood that the particulars shown are by way of example and for purpose of illustrative discussion of preferred embodiments of the invention.

EXAMPLES

In literature methods have been reported to synthesize alkyl carbamates by various routes. In the present invention, synthesis has been done by non-catalytic route using urea and alcohol. Simple tubular reactor has been used to conduct the said reaction.

(A) Urea+Methanol

Solution of Urea and corresponding alcohol was prepared and pumped through the tubular reactor of ½" tube. In all of the experiments, 1000 g urea was dissolved into 7470 g methanol to obtain homogeneous solution. This proportion was maintained throughout the experiment. Temperature inside the reactor was maintained by heating the reactor wall from outside by electrical heaters. No special rotating equipments are required which makes the operation very simple and inexpensive compared to other routes and corresponding equipments. Since the reaction is reversible, higher molar feed ratio of alcohol to urea was used to drive the reaction forward. The ammonia formed during reaction was removed by stripping, which drove reaction further thereby obtaining near complete conversion of urea. At steady state ~90% urea conversion and ~97% selectivity could be obtained consistently in first pass.

Example 1

1000 g urea was dissolved into 7470 g methanol to obtain homogeneous solution. The said mixture was subsequently pumped into a tubular reactor of ½" outer diameter (ASTM A269) using HPLC pump, the pumping rate being 5 ml/min. The typical length of the reactor for this experiment was chosen to be 4 meters. The temperature inside the reactor was maintained at 170° C. The pressure of the reactor was maintained at 22.5 bar using the back pressure regulator mounted downstream of the tubular reactor. Cumulative samples were collected after experiments and were analyzed using GC and HPLC to quantify raw materials and products. HPLC analysis showed 81.4% urea conversion and GC analysis showed 96.6% MC selectivity.

The ASPEN simulations of a configuration of tubular reactor—stripper—tubular reactor clearly demonstrate the advantage of the disclosed configurations.

Example 2

Experimental Procedure and Results

The individual weights of ingredients in urea—methanol mixture were kept unchanged from Example 1. Similarly, the dimensions of the reactor, temperature inside reactor and the flow rate of the mixture were kept unchanged. The change from the Example 1 was the pressure of the reactor, which was maintained at 23 bar using back pressure regulator mounted downstream of the tubular reactor. HPLC analysis showed 78.4% urea conversion and GC analysis showed 95.8% MC selectivity.

Example 3

The mixture of the ingredients, the temperature inside the reactor and the dimensions of the reactor were kept unchanged. However, the reaction feed comprising of urea and methanol mixture was pumped at flow rate of 7.5 ml/min through the reactor. The pressure of the reactor was maintained at 22.8 bar using back pressure regulator mounted downstream of the tubular reactor. HPLC analysis showed 69% urea conversion and GC analysis showed 94% MC selectivity.

Example 4

The ingredient mixture and the dimensions of the reactor were kept unchanged. In this example, the temperature inside the reactor was maintained at 180° C. The flow rate of urea and methanol mixture was kept 7.5 ml/min through the reactor, as in the Example 3. The pressure of the reactor was maintained at 28.5 bar using back pressure regulator mounted downstream of the tubular reactor. HPLC analysis showed 76% urea conversion and GC analysis showed 92.5% MC selectivity.

Example 5

In this example, the typical length of the reactor was chosen to be 9 meters. The temperature inside the reactor was maintained at 180° C. The flow rate of urea and methanol mixture was adjusted at 12.3 ml/min through the reactor. The pressure of the reactor was maintained at 28 bar. HPLC analysis showed 64% urea conversion and GC analysis showed 88% MC selectivity.

Example 6

The typical length of the reactor and the temperature of the reactor were kept unchanged from Example 5. The mixture of urea and methanol was pumped at flow rate of 6.2 ml/min through the reactor. The pressure of the reactor was maintained at 28 bar using back pressure regulator mounted downstream of the tubular reactor. HPLC analysis showed 79% urea conversion and GC analysis showed 90% MC selectivity.

Example 7

In this example, the only variable was the flow rate which was kept at 24.6 ml/min through the reactor. The pressure of the reactor was maintained at 28 bar. HPLC analysis showed 53% urea conversion and GC analysis showed 88% MC selectivity.

Example 8

The temperature inside the reactor was maintained at 170° C. The flow rate of the mixture was chosen to be 18 ml/min through the reactor. The pressure of the reactor was maintained at 23 bar. HPLC analysis showed 88.3% urea conversion and GC analysis showed 92.9% MC selectivity.

Example 9

The typical length of the reactor was unchanged 9 meter. The temperature inside the reactor was maintained at 170° C. The reaction flow rate was selected to be 18 ml/min through the reactor. The pressure of the reactor was maintained at 23 bar. HPLC analysis showed 93% urea conversion and GC analysis showed 99.4% MC selectivity.

Example 10

In Example 10, all of the variables were same as in Example 8 and 9. HPLC analysis showed 90.8% urea conversion and GC analysis showed 97.2% MC selectivity.

The data of aforesaid experiments is shown below in table 1

| Experiment No. | Reactor length [m] | Feed flow rate [ml/min] | Temperature [° C.] | Pressure [bar] | Urea conversion [%] | MC selectivity [%] |
|---|---|---|---|---|---|---|
| 1 | 4 | 5 | 170 | 22.5 | 81.4 | 96.6 |
| 2 | 4 | 5 | 170 | 23 | 78.4 | 95.8 |
| 3 | 4 | 7.5 | 170 | 22.8 | 69 | 94 |
| 4 | 4 | 7.5 | 180 | 28.5 | 76 | 92.5 |
| 5 | 9 | 12.3 | 180 | 28 | 64 | 88 |
| 6 | 9 | 6.2 | 180 | 28 | 79 | 90 |
| 7 | 9 | 24.6 | 180 | 28 | 53 | 88 |
| 8 | 9 | 18 | 170 | 23 | 88.3 | 92.9 |
| 9 | 9 | 18 | 170 | 23 | 93 | 99.4 |
| 10 | 9 | 18 | 170 | 23 | 90.8 | 97.2 |

(B) Other than Methanol

Instead of methanol, urea was dissolved into ethanol, propanol and butanol in different proportions. The outer diameter of the tubular reactor was ½" whereas the reactor length was chosen to be 4 meters throughout the experiment. The mixture is maintained between 185-190 degree.

Example 11

250 g urea was dissolved into 7500 g propanol to obtain homogeneous solution. This mixture was subsequently pumped into a tubular reactor of ½" outer diameter (ASTM A269) using HPLC pump at a flow rate of 18 ml/min through the reactor. The typical length of the reactor for this experiment was 4 meter. The temperature inside the reactor was maintained at 185 to 190° C. The pressure of the reactor was maintained at 15 bar using back pressure regulator mounted downstream of the tubular reactor. The process was carried out for 8 hours. Cumulative samples were collected after experiments and were analyzed with the help of GC and HPLC to quantify raw materials and products. HPLC analysis showed 96.7% urea conversion and GC analysis showed 95.7% propyl carbamate selectivity.

Example 12

500 g urea was dissolved into 7666 g ethanol to obtain homogeneous solution. This mixture was pumped into a tubular reactor at flow rate of 18 ml/min through the reactor. The pressure of the reactor was maintained at 25 bar using back pressure regulator mounted downstream of the tubular reactor. The reaction was carried out for 8 hours. HPLC analysis showed 95.2% urea conversion and GC analysis showed 74.3% ethyl carbamate selectivity.

Example 13

134 g urea was dissolved into 6621 g butanol to obtain homogeneous solution. This mixture was then at flow rate of 18 ml/min through the reactor. The pressure of the reactor was maintained at 8 bar. The reaction was carried out for 7 hours. HPLC analysis showed 92.8% urea conversion and GC analysis showed 77.4% BC selectivity.

The data of the aforesaid examples are tabulated in Table 2:

| Exp. No. | Reactor length [m] | Feed flow rate [ml/min] | Temperature [° C.] | Time (h) | Pressure [bar] | Urea conversion [%] | Alkyl Carbamate selectivity [%] |
|---|---|---|---|---|---|---|---|
| 1 | 4 | 18 | 185 to 190 | 8 | 15 | 96.7 | Propyl carbamate = 95.7 |
| 2 | 4 | 18 | 185 to 190 | 8 | 25 | 95.2 | Ethyl carbamate = 74.3 |
| 3 | 4 | 18 | 185 to 190 | 7 | 8 | 92.8 | Butyl carbamate = 77.4 |

The invention claimed is:

1. A catalyst free process for synthesis of alkyl carbamate within an integrated system of at least one tubular reactor and a stripper in series, comprising: (1) reacting urea and an alcohol in said tubular reactor under autogenous pressure, (2) pumping the mixture of step (1) into a tubular reactor with a pump at a feed rate in the range of 2-25 ml/min; and (3) maintaining the pressure of the reactor of step (2) using a back pressure regulator mounted downstream from the tubular reactor and collecting the desired carbamate, wherein said process provides >90% selectivity towards alkyl carbamate, wherein the alcohol is selected from methanol, ethanol, 1-propanol, 2-propanol, 1-butanol, 2-butanol, tert-butanol, pentanol, and hexanol.

2. The catalyst free process according to claim 1, wherein the temperature of the reaction mixture is in the range of 150-250° C.

3. The catalyst free process according to claim 1, wherein urea and alcohol in mole ratio 10 to 50 are fed in to the tubular reactor at a feed rate of 5-25 ml/min and a residence time less than 1 hour.

4. The catalyst free process according to claim 1, wherein said process can be carried out continuously, semi continuously or batch wise.

5. The catalyst free process according to claim 1, wherein the process further comprises reacting said alkyl carbamate with an alcohol to obtain dialkyl carbonate in said integrated system.

6. An integrated system for a catalyst free process for the synthesis of alkyl carbamate as claimed in claim 1 comprising at least one tubular reactor, heated externally, for reacting urea and alcohol and a stripper for removal of ammonia formed during the said process, wherein said tubular reactor and said stripper are arranged in series to reduce the equilibrium limitations of the reaction and drive the reaction in forward direction.

7. The integrated system according to claim 6, further comprises DMC reactor, wherein said alkyl carbamate obtained is reacted with alcohol vapors to obtain dialkyl carbonates.

8. The integrated system according to claim 6, wherein the diameter of the tubular reactors is ½" and the length is in the range of 4 to 9 meters to achieve adequate residence time and high conversion rate of urea.

9. The integrated system according to claim 6, wherein the temperature of the tubular reactor is in the range 150-250° C.

* * * * *